United States Patent [19]
Fischer

[11] Patent Number: 4,551,100
[45] Date of Patent: Nov. 5, 1985

[54] METHOD OF PREPARING GINGIVAL AREA FOR DENTAL CROWNS

[75] Inventor: Dan E. Fischer, Salt Lake City, Utah

[73] Assignee: Ultradent, Inc., Salt Lake City, Utah

[21] Appl. No.: 613,044

[22] Filed: May 22, 1984

Related U.S. Application Data

[63] Continuation of Ser. No. 386,103, Jun. 7, 1982, abandoned.

[51] Int. Cl.$^4$ ................................................. A61K 5/00
[52] U.S. Cl. .................................... 433/218; 424/147; 604/3; 604/11
[58] Field of Search ............. 424/147; 604/3, 11; 433/218

[56] References Cited

U.S. PATENT DOCUMENTS

| | | |
|---|---|---|
| 459,738 | 7/1891 | Black .................................. 424/147 |
| 977,825 | 12/1910 | Murphy . |
| 1,908,403 | 5/1933 | Budde . |
| 2,209,454 | 7/1940 | Griest ................................ 424/147 |
| 2,322,735 | 6/1943 | Molnar ............................... 424/147 |
| 2,411,636 | 11/1946 | Preiswerk ......................... 424/147 |
| 3,175,242 | 3/1965 | Kamondy et al. . |
| 3,234,918 | 2/1966 | Gigli . |
| 3,369,543 | 2/1968 | Ronco . |
| 3,434,209 | 3/1969 | Weissman . |
| 3,759,259 | 9/1973 | Truhan .............................. 604/3 |
| 4,157,709 | 6/1979 | Schuster et al. . |

OTHER PUBLICATIONS

"Clinical Research Associates Newsletter", Aug. 1979, pp. 2 and 3.
"Restorative Techniques for Individual Teeth", edited by Lloyd Baum, Masson Publishing USA, Inc., (1981), Chapter 15.
"Dental Products Reports", Jul.-Aug. issue, 1981, advertisement p. 11.

*Primary Examiner*—George F. Lesmes
*Assistant Examiner*—Nancy A. B. Swisher
*Attorney, Agent, or Firm*—Workman, Nydegger & Jensen

[57] ABSTRACT

A method for controlling or stopping the flow of blood is provided for use in preparing the gingival or gum area of the mouth for dental crowns. An aqueous solution of ferric sulfate ($Fe_2(SO_4)_3$), having a concentration of preferably about 13% in water and glycol. The solution is applied to the gingival area and rapidly coagulates fresh blood to act as an effective astringent without adverse side effects or staining of teeth.

4 Claims, No Drawings

METHOD OF PREPARING GINGIVAL AREA FOR DENTAL CROWNS

This is a continuation of application Ser. No. 06/386,103, filed June 7, 1982, now abandoned.

BACKGROUND OF THE INVENTION

One of the primary concerns in dentistry is the controlling of oral bleeding during dental operative procedures, such as oral surgery, taking impressions of teeth for reconstruction, and the like. For example, in the field of dental reconstruction or preparation of dental crowns, it is common for dentists to cut gingival or gum tissue in order to fully expose the tooth prior to taking an impression of the tooth. It is imperative that the area surrounding the tooth be clean and dry for an accurate impression to be made. To this end, various hemostatic agents have been commonly used to stop bleeding.

One of the most common hemostatic agents in use today in the dental field is an aqueous solution of aluminum chloride, marketed under a variety of tradenames by several manufacturers. Another product in use today as a hemostatic agent is a vasoconstrictor known as epinephrine. However, epinephrine can produce serious cardiovascular effects such as a speeding heart rate, and its use has been questioned in such publications as *Accepted Dental Therapuetics*, 37th Edition, as an acceptable hemostat. Aqueous solutions of aluminum chloride are not as effective as could be desired and produce a very undesirable taste in the patient's mouth.

Consequently, there has been a need for a more effective method of preparing gingival areas and for a hemostatic agent having rapid coagulant and astringent characteristics. While iron salts in general have been recognized as having certain astringent characteristics, they have heretofore been characterized as ineffective as coagulants and been found objectionable due to the yellow staining of teeth and the high acidity of the salt solution causing potential corrosion to tooth enamel. See for example, *Accepted Dental Therapeutics*, 37th Edition, Page 220.

It is an objective of this invention to provide a method for preparing gingival areas of the mouth for dental reconstruction by using a ferric sulfate solution which acts as a coagulant and astringent without damaging side effects, such as staining of tooth enamel and corrosion of teeth.

BRIEF SUMMARY OF THE INVENTION

The objective of this invention is achieved by preparing an aqueous solution of ferric sulfate ($Fe_2(SO_4)_3$) for use in the gingival area as a hemostatic agent having both coagulant and astringent properties. The solution is prepared with preferably about 13% concentration of ferric sulfate in water and glycol.

DETAILED DESCRIPTION OF THE PREFERRED EMBODIMENT

In a preferred embodiment, the preparation of the preferred hemostatic solution for use in the method is to provide a concentration of ferric sulfate of approximately 13%. It has been found that 13% is the optimum concentration, because lesser concentrations evidence a progressively diminished amount of hemostatic activity, until at about 6% the activity becomes ineffective. At the other end, it has been found that concentrations above about 20% show slower increase in hemostatic activity. Solutions above about 40% ferric sulfate exhibit only a slight increase in activity.

It is important not to confuse this solution with a well-known material called Monsel's Solution which is a ferric subsulfate suspension. Ferric subsulfate has a different chemical composition. Monsel's is actually a suspension rather than a solution. It has a percent acidity of 72% compared to 10.1% acidity for the 13.3% ferric sulfate solution of the present invention.

The aqueous solution of the invention has been found in clinical testing to be very effective in controlling external bleeding. It has also been shown to be tolerated better than the prior art hemostats by patients and to avoid the unbearable taste of the aluminum chloride.

In vitro tests were conducted using fresh blood on glass slides. A ferric sulfate solution was prepared in accordance with the invention using distilled water, and the solution was sterilized by heating the solution under 20 lbs. pressure for 30 minutes in a steam autoclave. A commercially available solution of aluminum chloride (25% concentration) was used as the standard to determine rate of coagulation. In each test four drops of fresh blood were applied to a glass slide followed by two drops of the sterilized ferric sulfate solution. The blood and solution were immediately mixed with a glass stirring rod and rated as to both rapidity and completion of coagulation. In each test, the ferric sulfate solution coagulated the blood more rapidly and more completely than did the aluminum chloride.

The solution is designed to aid in the control of bleeding and can be applied in a number of ways.

It may be applied to the gingival area of the mouth with an applicator, such as the Dento-Infuser which slowly applies the solution with or without pressure to a small area of bleeding to control bleeding. If used with this device, the solution is simply loaded into the syringe, or prefilled carpules are employed. The tip of the applicator is then inserted into the bleeding wound site, be it a cut, gingival sulcus, pulp chambers, (as in pulpotomies on primary teeth) or the like. By "burnishing" or rubbing the end of the applicator at the same time the solution is deposited the bleeding can readily be controlled. It is wise not to use more solution than needed, therefore, this device lends itself well to the application.

When preparing to take an impression of a tooth to fabricate a crown restoration, the crevice (sulcus) between the tooth and gum is packed with a filament cord. This distends the tissue slightly from the tooth so that the impression material may enter, and controls any bleeding so that an accurate impression may be obtained. If the cord is first soaked in the ferric sulfate solution, the hemostats and retraction is greatly enhanced. This may be accomplished at the time the tooth is prepared or retraction cord may be pre-soaked with solution and dried to produce a "hemostatic cord" ready for immediate use.

Like many other medicaments, the solution can be applied with small cotton pledgets. The cotton pledgets are simply soaked in the solution to moisten them. They are then placed to whatever location is desired to control bleeding whether bleeding gingiva (gums), bleeding pulp chambers, or any other wound area whether in dentistry or medicine.

Tests were undertaken on extracted teeth to determine whether the acidity and yellow-staining properties of the solution would have any effect on its use as a hemostatis agent.

Both the ferric sulfate solution and the aluminum chloride solution are acidic, having approximately equivalent pH. Since they are acidic, they have the potential of decalcifying enamel. The length of time of exposure to the enamel would be a limiting factor. At the present time, dentists will many times purposely etch enamel by decalcifying the surface with a fairly strong acid, one strong enough to procuce a chalky appearance to the enamel within 30-60 seconds. This is done to promote the bonding of new adhesive type restorations to the enamel. The etching doesn't penetrate to any harmful depth, however, as enamel luster can be regained by simply polishing the surface. For these tests, samples of clean extracted teeth were immersed in water, aluminum chloride and the ferric sulfate solution of the invention for a period of one hour. Upon removing and drying, the aluminum choride and ferric sulfate samples appeared chalky on the surface, much as a tooth etched for applying an adhesive type restoration. Upon polishing the samples with pumice and a rubber cup in the same fashion as a patient's teeth are polished, the chalkiness disappeared, and the teeth once again appeared as the control samples which were placed in water.

Ferric sulfates appear yellow in solution and will temporarily yellow or stain soft tissue until it is cleaned off. It would be imperative, however, that no permanent staining occur with the use of the ferric sulfate solution against enamel. Using the same samples as mentioned above, another test was run to determine any change of color. A chromoscan produced by APM Sterngold was used to measure the amount of the three basic colors (e.g. red, green, and blue) of the samples prior to any treatment. The samples were immersed for one hour in their respective solutions, ferric sulfate, aluminum chloride, and water, after which new chromoscan readings were taken. The chromoscan gave a digital three unit readout for all three colors. This test would indicate not only the cosmetic importance of maintaining original tooth color, but it would also indicate any corrosive change or permanent decalcification.

There was little change on any of the three samples. Aluminum chloride had a change of 0.6 units on the chromoscan readout from water (the control group) and the ferric sulfate solution had a change of 0.1. The chromoscan requies a change of 8 to 15 units before any significant visual change is observable. Neither agent can be said to have any significant visual effect on tooth color.

Clinical tests over a six year period have shown that the method of the invention using the hemostatic agent is effective in producing minimal tissue irritation and less sloughage and destruction of tissue than with aluminum chloride solutions and epinephrine-type agents.

While this invention has been described in a preferred embodiment, it will be understood that there are substantial equivalents which fall with the scope of the appended claims.

I claim:

1. A method for halting bleeding in gingival tissue preparatory to the taking of dental impressions, comprising the steps of:

providing an applicator device capable of applying a hemostatic solution of aqueous ferric sulfate ($Fe_2(SO_4)_3$) having a concentration in the range of about 6 percent to about 20 percent under pressure to an area of bleeding gingival tissue, said applicator device having a padded porous tip through which hemostatic solution may be applied;

inserting the tip of the applicator into a bleeding wound site;

placing the tip of the applicator device against bleeding tissue;

dispensing the hemostatic agent from the tip of the applicator device under pressure onto bleeding tissue; and burnishing the bleeding tissue while simultaneously dispensing the hemostatic agent under pressure so as to halt bleeding of such tissue.

2. A method for halting bleeding in gingival tissue preparatory to the taking dental impressions as defined in claim 1, wherein the aqueous ferric sulfate solution has a ferric sulfate concentration of about 13 percent.

3. A method for halting bleeding in gingival tissue preparatory to the taking dental impressions, comprising the steps of:

providing an applicator device capable of controlled dispensing of an aqueous ferric sulfate ($Fe_2(SO_4)_3$) solution having a concentration in the range of about 6 percent to about 20 percent through a padded tip of the applicator to an area of bleeding gingival tissue;

placing the tip of the applicator device against the bleeding gingival tissue;

dispensing the ferric sulfate solution into the bleeding tissue; and burnishing the bleeding gingival tissue with the tip of the applicator device while dispensing the ferric sulfate solution so as to halt bleeding of such tissue.

4. A method for halting bleeding in gingival tissue preparatory to the taking dental impressions as defined in claim 3, wherein the aqueous ferric sulfate solution has a ferric sulfate concentration of about 13 percent.

* * * * *

UNITED STATES PATENT AND TRADEMARK OFFICE
CERTIFICATE OF CORRECTION

PATENT NO.   :   4,551,100

DATED        :   November 5, 1985

INVENTOR(S)  :   Dan E. Fischer

It is certified that error appears in the above-identified patent and that said Letters Patent is hereby corrected as shown below:

```
     Column 1, line 28, "Therapuetics" should be --Therapeutics--
     Column 2, line 53, "hemostats" should be --hemostatis--
     Column 3, line 47, "requies" should be --requires--
     Column 4, line 5, "with the" should be --within the--
     Column 4, line 29, "taking dental" should be --taking of
dental--
     Column 4, line 33, "taking dental" should be --taking of
dental--
     Column 4, line 50, "taking dental" should be --taking of
dental--
```

Signed and Sealed this

Fourth Day of March 1986

[SEAL]

Attest:

DONALD J. QUIGG

Attesting Officer

Commissioner of Patents and Trademarks